United States Patent [19]
Chen et al.

[11] Patent Number: 5,888,923
[45] Date of Patent: Mar. 30, 1999

[54] MODIFIED RANEY NICKEL CATALYST AND A PROCESS FOR PREPARING DIOLS BY USING THE SAME

[75] Inventors: Shien Chang Chen, Taipei; C. C. Chu, Kaohsiung; F. S. Lin, Kaohsiung; J. Y. Chou, Kaohsiung; C. C. Huang, Kaohsiung, all of Taiwan

[73] Assignee: Dairen Chemical Corporation, Taipei, Taiwan

[21] Appl. No.: 632,600

[22] Filed: Apr. 15, 1996

[51] Int. Cl.[6] ....................................... B01J 25/00
[52] U.S. Cl. ......................... 502/301; 502/150; 502/173; 502/335; 568/459; 568/461; 568/388; 568/877; 568/875; 568/828
[58] Field of Search ................................. 502/150, 301, 502/335; 568/459, 361, 388, 877, 675, 828

[56] References Cited

U.S. PATENT DOCUMENTS

| | | | |
|---|---|---|---|
| 3,144,490 | 8/1964 | Rylander et al. | 260/718 |
| 3,673,116 | 6/1972 | Richter | 252/466 T |
| 3,896,051 | 7/1975 | Mabuchi et al. | 252/412 |
| 3,980,720 | 9/1976 | Mabuchi et al. | 252/412 |
| 3,997,478 | 12/1976 | Petro | 252/470 |
| 4,036,895 | 7/1977 | Vogel et al. | 260/63 R |
| 4,043,946 | 8/1977 | Sanker et al. | 258/466 J |
| 4,049,580 | 9/1977 | Oden et al. | 257/466 J |
| 4,110,257 | 8/1978 | Ottare | 257/466 J |
| 4,153,578 | 5/1979 | DeThomas et al. | 252/438 |
| 4,166,805 | 9/1979 | Jewett | 252/430 |
| 5,063,184 | 11/1991 | Jewett | 502/150 |

FOREIGN PATENT DOCUMENTS 659981   10/1931   United Kingdom .

OTHER PUBLICATIONS

*Biochemistry Journal,* "Studies in the Biochemistry of Micro–organisms," J.H. Birkinshaw, A. Bracken and H. Raistrick, 1943, vol. 37, pp. 726–729.

*Journal of American Chemical Society,* "Tetrahydrocannabinol Homologs with Doubly Branched Alkyl Groups in the 3–Position. XVIII", Roger Adams, Scott MacKenzie, Jr. and S. Loewe, 1948, vol. 70, pp. 664–669.

*Journal of Organic Chemistry,* "Rhenium and Its Compounds as Hydrogenation Catalysts. III. Rhenium Heptoxide[1,2,3]," 1959, vol. 24, pp. 1847–1854.

*Industrial and Engineering Chemistry,* "Vapor–Phase Nitration of Neopentane and Neohexane," A.P. Howe and H.B. Hass, 1946, vol. 38, pp. 251–253.

"High Pressure Reduction of Glucose or Fructose or Sucrose to Sorbitol," S. Yamamoto (English Abstract of Article), *Journal of Chemical Society, Japan, Industrial Chemistry Section,* 1943, vol. 49, pp. 901–903.

*Journal of Chemical Society,* "The Preparation of Raney Nickel Catalysts and their Use Under Conditions Comparable with Those for Platinum and Palladium Catalysts," Homer Adkins and Harry R. Billica, 1948, vol. 70, pp. 695–698.

*Journal of Applied Chemistry,* "Raney Cobalt Hydrogenation Catalysts. III. Applications and Promoter Effects," B.V. Aller, 1958, vol. 8, pp. 492–495.

*Primary Examiner*—Helane Myers
*Attorney, Agent, or Firm*—Smith, Gambrell & Russell, LLP; Beveridge, DeGrandi, Weilacher & Young Intellectual Property Group

[57] ABSTRACT

The present invention relates to a modified Raney nickel catalyst which can serves as hydrogenation catalyst for hydroxy aldehydes, such as 4-hydroxy-butanal, and 2-methyl-3-hydroxypropanal and hydroxy cyclic ethers such as 2-hydroxy-tetrahydrofuran. Further, a process for preparing diols by using the modified Raney nickel catalyst is provided.

13 Claims, No Drawings

MODIFIED RANEY NICKEL CATALYST AND A PROCESS FOR PREPARING DIOLS BY USING THE SAME

FIELD OF THE INVENTION

The present invention relates to a modified Raney nickel catalyst and a process for preparing diols by using the modified Raney nickel catalyst.

BACKGROUND OF THE INVENTION

Conventionally, 4-hydroxy-butanal 2-hydroxy-tetrahydrofuran, and 2-methyl-3-hydroxypropanal are industrially prepared by hydroformylating allyl alcohol, carbon monoxide, and hydrogen in the presence of rhodium as a catalyst The reactions of the conventional processes are shown as follows:

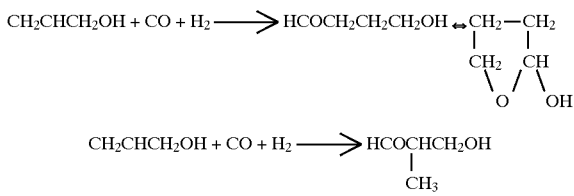

4-hydroxy-butanal and 2-hydroxy-tetrahydrofuran can be used for producing 1,4-butanediol through hydrogenation while 2-methyl-3-hydroxypropanal can be used for producing 2-methyl-1,3-propanediol through hydrogenation. The reactions thereof are shown as follows:

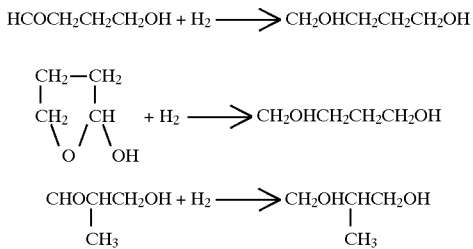

The hydrogenation of 4-hydroxy-butanal and 2-methyl-3-hydroxypropanal is subject to hydrogenation of carbonyl group. Presently, the catalyst used in the process of hydrogenation of carbonyl group is selected from precious metals including palladium, which is disclosed in *Biochemistry Journal*, 1943, Vol. 37, p.726; platinum which is disclosed in *Journal of American Chemical Society*, 1948, Vol. 70, p.664; ruthenium, which is disclosed in U.S. Pat. No. 3,144,490; rhenium, which is disclosed in *Journal of Organic Chemistry*, 1959, Vol. 24, p.1847; copper chromite, which is disclosed in *Industrial and Engineering Chemistry*, 1946, Vol. 38, p.251; copper, which is disclosed in British Patent No. 659,981; nickel, which is disclosed in *Journal of Chemical Society, Japan, Industrial Chemistry Section*, 1943, Vol. 46, p.901; Raney nickel, which is disclosed in *Journal of American Chemical Society*, 1948, Vol. 70, p.695; Raney cobalt, which is disclosed in *Journal of Applied Chemistry*, 1958, Vol. 8, p.492; and so on.

Through long-term experiments, it has been found by the inventors that the hydrogenations of 4-hydroxy-butanal, 2-hydroxy-tetrahydrofuran, and 2-methyl-3-hydroxypropanal differ from that of other carbonyl groups. For instance, the use of palladium or zinc copper oxide as catalyst shows almost no reaction activity; and the use of ruthenium or copper chromite as catalyst shows only relatively low reaction activity to the hydrogenation which provides little utilization value. Only nickel and Raney nickel provide higher reaction activity to the hydrogenation. However, it has been subsequently found a drawback to the use of nickel or Raney nickel as catalyst in the aforementioned hydrogenation process in that their reaction activity rapidly decay after repetitive uses. More specifically, after batchwise repetitive uses exceeding 33 batches or continuous use exceeding 30 hours, their reaction activity significantly decreases to a low level that can't practically be used further. Accordingly, the use of nickel or Raney nickel as catalyst in the hydrogenation process for producing 1,4-butanediol, 2-methyl-1,3-propanediol from 4-hydroxy-butanal, 2-hydroxy-tetrahydrofuran, and 2-methyl-3-hydroxypropanal is still not a practical approach in the chemical industry.

SUMMARY OF THE INVENTION

It is therefore a primary objective of the present invention to provide a modified Raney nickel catalyst which is of high and long-lasting reaction activity for the hydrogenation of 4-hydroxy-butanal, 2-hydroxy-tetrahydrofuran, and 2-methyl-3-hydroxypropanal.

It is another objective of the present invention to provide an improved process for preparing diols by using the modified Raney nickel catalyst.

In accordance with the foregoing and other objectives of the present invention, there is provided with a modified Raney nickel catalyst and a process for preparing diols by using the modified Raney nickel catalyst. It is found through experiments that Raney nickel modified by the addition of iron or iron and at least one metal selected from the group consisting of chromium, molybdenum, tungsten, cobalt, manganese, and titanium shows a relatively high reaction activity to the process for preparing diols and allows long-term use thereof as the catalyst for the process for preparing diols. The provision of the catalyst according to the present invention thus enables the preparation of 1,4-butanediol and 2-methyl 1,3-propanediol through hydrogenation of 4-hydroxy-butanal, 2-hydroxy-tetrahydrofuran, and 2-methyl-3-hydroxypropanal to have high commercial value.

DETAILED DESCRIPTION OF THE INVENTION

The modified Raney nickel catalyst according to the present invention consists essentially of 40–98 wt % of nickel 1–50 wt % of aluminum, and 0.05–15 wt % of iron. If necessary, the modified Raney nickel catalyst can be further added with 0.05–10 wt % of at least one metal selected from the group consisting of chromium molybdenum, tungsten cobalt, manganese, and titanium.

Process for producing the modified Raney nickel catalyst according to the present invention is essentially similar to conventional ones for producing Raney nickel catalyst Typically, predetermined amounts of nickel, aluminum, and iron are mixed first and, if necessary, at least one metal selected from the group consisting of chromium, molybdenum, tungsten, cobalt, manganese, and titanium may be added thereto. The mixture is then melted at a temperature of 1200° to 2000° C. to produce a precursor alloy. After being sat still and cooled, the precursor alloy is crushed into powder or granule with suitable size and then developed in a solution of alkali metal hydroxide. Finally, the thus-obtained product is washed with distilled or ion-exchanged water to obtain the modified Raney nickel catalyst.

The modified Raney nickel catalyst according to the present invention is useful as catalyst in the hydrogenation of hydroxy aldehydes, particularly 4-hydroxy-butanal 2-hydroxy-tetrahydrofuran, and 2-methyl-3-hydroxypropanal.

Moreover, the modified Raney nickel catalyst according to the present invention can be used in a process for producing diols. In the process, hydroxy aldehyde is hydrogenated under a temperature of 50° to 200° C., preferably 75 to 150° C., and a pressure of 10 to 200 kg/cm$^2$G, preferably 20 to 80 kg/cm$^2$G to obtain diols.

In the foregoing process, the reactor used therefor depends on the form of the catalyst used. If the catalyst is powder type, then a slurry bed reactor is used; while if the catalyst is granule type, a fixed bed reactor is used. The process can be proceeding continuously or batchwisely.

In the case of slurry bed reactor, the amount of the catalyst used is 0.5–20 wt % based on the total weight of solution; and in the case of fixed bed reactor, the liquid hourly space velocity (LHSV) is 0.1 to 10 hr$^{-1}$.

In the process according to the present invention, the hydroxy aldehyde used can be 4-hydroxy-butanal, 2-hydroxy-tetrahydrofuran, or 2-methyl-3-hydroxypropanal.

It is a primary benefit of the modified Raney nickel catalyst according to the present invention tat it is of high reaction activity and long use life.

Examples used to illustrate the present invention are respectively carried out in slurry bed reactor and fixed bed reactor and described in the following. It is to be understood that the scope of the present invention is not to be limited by the following disclosed examples.

1. Experiments with Slurry Bed Reactor

EXAMPLE 1

0.781 g of carbonylhydrotis(triphenyl phosphine) rhodium, 21.6 g of triphenyl phosphine, 55.4 g of allyl alcohol, and 73.6 g of toluene were charged to a pressure-resistant glass stirring reactor controlled at a temperature of 60° C. and filled with carbon monoxide and hydrogen (in a molar ratio of 1) to have a pressure of 7 kg(cm$^2$G to carry out hydroformylation for a period of 6.5 hours. Then the solution was extracted by deionized water to obtain a top layer of toluene solution containing hydroformylation catalyst and a bottom layer of aqueous solution containing 4-hydroxy-butanal, 2-hydroxy-tetrahydrofuran, and 2-methyl-3-hydroxypropanal.

An alloy containing 38.5 wt % of nickel (Ni), 58.4 wt % of aluminum (Al), 1.4 wt % of iron (Fe), and 1.7 wt % of chromium (Cr) was melted at a temperature of 1650° C. After cooled, the thus-obtained alloy was granulated to a granularity of 20–150 $\mu$m. 30 g of sodium hydroxide was then dissolved in 150 ml of water under stirring while the temperature was lowered to 50 to 60° C. 20 g of the alloy powder was added to the sodium hydroxide solution and the thus-obtained solution was then heated to a temperature of 50° to 100° C. followed by stirring for a period of 30 to 120 minutes to disperse the alloy powder. After dispersed, the solution was washed with deionized water until the pH of the washings was in the range between 8 and 9. Then a Raney nickel catalyst for hydrogenation containing 85 wt % of nickel (Ni), 9.5 wt % of aluminum (Al), 2.5 wt % of iron (Fe), and 3.0 wt % of chromium (Cr) was obtained.

420 ml of the solution containing 4-hydroxy-butanal, 2-hydroxy-tetrahydrofuran, and 2-methyl-3-hydroxypropanal was charged to a stainless jacket-stirring reactor equipped with a metal powder-sintered filtering core followed by adding 9.38 g of the thus-obtained hydrogenation catalyst (65% of which has a granularity less than 50 $\mu$m). A temperature in the reactor was controlled at 115° C. and a pressure in the reactor was maintained at 60 kg/cm$^2$G by the supply of hydrogen to effect hydrogenation for 2 hours under stirring. After the supply of hydrogen was cut off, the stirring was stopped and the solution was set still for 30 minutes to precipitate the catalyst. The solution was filtrated via the filtering core by the hydrogen pressure in the reactor, then about 400 ml of the top layer of the solution was removed and analyzed by gas chromatograph to obtain a result of 16.64 wt % of 1,4-butanediol, 3.25 wt % of 2-methyl-1,3-propanediol, 80.11 wt % of other reactants and water. Another 400 ml aqueous solution of 4-hydroxy-butanal, 2-hydroxy-tetrahydrofuran, and 2-methyl-3-hydroxypropanal was then added to the reactor and subjected to hydrogenation for 2 hours under the same condition. This process was repeated for 50 batches. The conversion thereof was maintained consistently at about 95–98%, which was calculated by the results obtained from gas chromatograph (GC) according to the following equation:

$$\text{Conversion} = \frac{HBA1 - HBA2}{HBA1} * 100\%$$

wherein

HBA1 represents the concentration of the solution of 4-hydroxy-butanal, 2-hydroxy-tetrahydrofuran, and 2-methyl-3-hydroxypropanal obtained ma GC analysis before hydrogenation; and HBA2 represents the concentration of the solution of 4-hydroxy-butanal, 2-hydroxy-tetrahydrofuran, and 2-methyl-3-hydroxypropanal obtained via GC analysis after hydrogenation.

EXAMPLE 2

Hydrogenation was carried out in the same manner as that of Example 1 except that 57% of the Raney nickel catalyst for hydrogenation were of a granularity of less than 50 $\mu$m and the composition of the catalyst consisted of 87.1 wt % of nickel (Ni), 9.9 wt % of aluminum (Al), and 3.0 wt % of iron (Fe). The process was repeated for 50 batches. The conversion was consistently maintained at about 93–98%.

EXAMPLE 3

Hydrogenation was carried out in the same manner as that of Example 1 except that 90% of the Raney nickel catalyst for hydrogenation were of a granularity of less than 87 $\mu$m and the composition of the catalyst consisted of 87.0 wt % of nickel (Ni), 9.9 wt % of aluminum (Al), 0.1 wt % of iron (Fe), and 3.0 wt % of chromium (Cr). The process was repeated for 46 batches. The conversion was consistently maintained at about 90–98%.

EXAMPLE 4

Hydrogenation was carried out in the same manner as that of Example 1 except that 90% of the Raney nickel catalyst for hydrogenation were of a granularity of less than 162 $\mu$m and the composition of the catalyst consisted of 92.0 wt % of nickel (Ni), 6.1 wt % of aluminum (Al), 0.7 wt % of iron (Fe), and 1.2 wt % of molybdenum (Mo). The process was repeated for 45 batches. The conversion was consistently maintained at about 90–98%.

EXAMPLE 5

Hydrogenation was carried out in the same manner as that of Example 1 except that 65% of the Raney nickel catalyst for hydrogenation were of a granularity of less than 50 μm and the composition of the catalyst consisted of 86.0 wt % of nickel (Ni), 9.5 wt % of aluminum (Al), 0.5 wt % of iron (Fe), 0.2 wt % of titanium (Ti), and 2.0 wt % of tungsten (W). The process was repeated for 40 batches. The conversion was consistently maintained at about 90–98%.

EXAMPLE 6

Hydrogenation was carried out in the same manner as that of Example 1 except that 46.8% of the Raney nickel catalyst for hydrogenation were of a granularity of less than 44 μm and the composition of the catalyst consisted of 87.0 wt % of nickel (Ni), 11.6 wt % of aluminum (Al), 1.2 wt % of iron (Fe), and 0.2 wt % of manganese (Mn). The process was repeated for 38 batches. The conversion was consistently maintained at about 90–98%.

COMPARATIVE EXAMPLE 1

Hydrogenation was carried out in the same manner as that of Exawple 1, except that 83.0% of the Raney nickel catalyst for hydrogenation were of a granularity of less than 50 μm and the composition of the catalyst consisted of 92.7 wt % of nickel (Ni), 6.1 wt % of aluminum (Al), and 1.2 wt % of molybdenum (Mo). The process was repeated for 33 batches. The conversion was then reduced from 90% to 70%.

COMPARATIVE EXAMPLE 2

Hydrogenation was carried out in the same manner as that of Example 1, except that the composition of the Raney nickel catalyst for hydrogenation consisted of 87.2 wt % of nickel (Ni), 3.6 wt % of aluminum (Al), and 9.2 wt % of manganese (Mn). The process was repeated for 15 batches. The conversion was reduced from 90% to 30%.

COMPARATIVE EXAMPLE 3

Hydrogenation was carried out in the same manner as that of Example 1, except that 60% of the Raney nickel catalyst for hydrogenation were of a granularity of less than 50 μm and the composition of the catalyst consisted of 92.7 wt % of nickel (Ni) and 7.3 wt % of aluminum (Al). The process was repeated for 10 batches. The conversion was reduced from 80% to 30%.

COMPARATIVE EXAMPLE 4

Hydrogenation was carried out in the same manner as that of Example 1, except that an RCH55/10 catalyst manufactured by the Hoechst Company of Germany was used. The RCH55/10 catalyst consists of 55 wt % of nickel (Ni) based on diatomaceous earth. The process was repeated for 3 batches. The conversion was reduced from 80% to 20%.

COMPARATIVE EXAMPLE 5

Hydrogenation was carried out in the same manner as that of Example 1, except that a Ni-1404P catalyst manufactured by the Harshaw company of USA was used. 100% of the Ni-1404P catalyst are of a granulaity of less than 100 μm and the composition of which consist of 66 wt % of nickel (Ni) based on $SiO_2$—$Al_2O_3$. The process was repeated for 3 batches. The conversion was reduced from 85% to 35%.

COMPARATIVE EXAMPLE 6

Hydrogenation was carried out in the same manner as that of Example 1, except that a 19A catalyst manufactured by the Johnson Matthey company of British was used. The 19A catalyst consists of 5 wt % of Ru based on active carbon. The process was carried out for just one batch and the conversion was only 16%.

COMPARATIVE EXAMPLE 7

Hydrogenation was carried out in the same manner as that of Example 1, except that an N-203SD catalyst manufactured by the Nikki company of Japan was used. The N-203SD catalyst consists of CuO and $Cr_2O_3$. The process was carried out for just one batch and the conversion was only 9%.

COMPARATIVE EXAMPLE 8

Hydrogenation was carried out in the same manner as that of Example 1, except that a G-66D catalyst manufactured by the Girdler company of Japan was used. The G-66D catalyst consists of 33 wt % of CuO and 65 wt % of ZnO. The process was carried out for just one batch and the conversion was 0%.

COMPARATIVE EXAMPLE 9

Hydrogenation was carried out in the same manner as that of Example 1, except that a catalyst manufactured by the Engelhard company of Japan was used. The catalyst consists of 2 wt % of Pd based on $Al_2O_3$. The process was carried out for just one batch and the conversion was 0%.

The results depicted in Examples 1–6 and Comparative Examples 1–9 are summarized in the table 1 below.

TABLE 1

(with slurry bed reactor)

| | Composition of the Catalyst (wt %) | Number of Batches | Conversion (%) |
|---|---|---|---|
| Example 1 | Ni:Al:Fe:Cr = (85):(9.5):(2.5):(3) | 50 | 95–98% |
| Example 2 | Ni:Al:Fe = (87.1):(9.9):(3) | 50 | 93–98% |
| Example 3 | Ni:Al:Fe:Cr = (87.0):(9.9):(0.1):(3) | 46 | 90–98% |
| Example 4 | Ni:Al:Fe:Mo = (92):(6.1):(0.7):(1.2) | 45 | 90–98% |
| Example 5 | Ni:Al:Fe:Ti:W = (86):(9.5):(0.5):(2):(2) | 40 | 90–98% |
| Example 6 | Ni:Al:Fe:Mn = (87):(11.6):(1.2):(0.2) | 38 | 90–98% |
| Comparative Example 1 | Ni:Al:Mo = (92.7):(6.1):(1.2) | 33 | reduced from 90% to 70% |
| Comparative Example 2 | Ni:Al:Mn = (87.2):(3.6):(9.2) | 15 | reduced from 90% to 30% |
| Comparative Example 3 | Ni:Al = (92.7):(7.3) | 10 | reduced from 80% to 30% |
| Comparative Example 4 | 55 wt % of nickel (Ni) based on diatomaceous earth | 3 | reduced from 80% to 20% |
| Comparative | 66 wt % of nickel (Ni) based on | 3 | reduced |

TABLE 1-continued (with slurry bed reactor)

| Composition of the Catalyst (wt %) | Number of Batches | Conversion (%) |
|---|---|---|
| Example 5 SiO$_2$—Al$_2$O$_3$ | | from 85% to 35% |
| Comparative Example 6  5 wt % of R based on active carbon | 1 | 16% |
| Comparative Example 7  CuO and Cr$_2$O$_3$ | 1 | 9% |
| Comparative Example 8  33 wt % of CuO and 65 wt % of ZnO | 1 | 0% |
| Comparative Example 9  2 wt % of Pd based on Al$_2$O$_3$ | 1 | 0% |

2. Experiments with Fixed Bed Reactor

EXAMPLE 7

0.781 g of carbonyl hydrotris (triphenyl phosphine) rhodium, 21.6 g of triphenyl phosphine, 55.4 g of allyl alcohol, and 73.6 g of toluene were charged to a pressure-resistant glass stirring reactor controlled at a temperature of 60° C. and a pressure of 7 kg/cm$^2$ G maintained by the supply of carbon monoxide and hydrogen with a molar ratio of 1 to carry out hydroformylation for 6.5 hours. Then the solution was extracted by deionized water to obtain a top layer of toluene solution containing hydroformylation catalyst and a bottom layer of aqueous solution containing 4-hydroxy-butanal, 2-hydroxy-tetrahydrofuran, and 2-methyl-3-hydroxypropanal.

To prepare hydrogenation catalyst, an alloy containing 40 wt % of nickel (Ni), 58 wt % of aluminum (Al), 0.5 wt % of iron (Fe), and 1.5 wt % of chromium (Cr) was melted at a temperature of 1650° C. After cooled, the thus-obtained alloy was granulated to a granularity of 3–10 mesh. 80 g of sodium hydroxide was then dissolved in 400 ml of water under stirring while the temperature was lowered to 50°–60° C. After that, 60 g of the granulated alloy was added to the sodium hydroxide solution which was then heated to a temperature of 50 °to 100° C. The solution was stirred for 30–120 minutes to disperse the alloy and then washed with pure water until the washing was of a pH in the range of 8 to 9. A Raney nickel catalyst for hydrogenation containing 57 wt % of nickel (Ni), 40.2 wt % of aluminum (Al), 0.7 wt % of iron (Fe), and 2.1 wt % of chromium (Cr) was thus obtained.

A solution of 4-hydroxy-butanal, 2-hydroxy-tetrahydrofuran, and 2-methyl-3-hydroxypropanal was pumped with a flow rate of 1.5 ml/min into a tubular reactor having a inner diameter of 1 cm. Inside the tubular reactor was there placed with 30 ml of the Raney nickel catalyst for hydrogenation. And the reactor was controlled at a temperature of 115° C. and a pressure of 60 kg/cm$^2$G maintained by the supply of hydrogen to carry out hydrogenation for one day, the thus-obtained solution was analyzed via gas chromatograph to find it of 17.38 wt % of 1,4-butanediol, 1.98 wt % of 2-methyl-1,3-propanediol, and 80.64 wt % of other reactants and water. The reaction was then continued for a period of 20 days. The conversion was consistently maintained at about 96–100%

EXAMPLE 8

Hydrogenation was carried out in the same manner as that of Example 7 except that a Raney nickel catalyst for hydrogenation consisting of 50.4 wt % of nickel (Ni), 47 wt % of aluminum (Al), and 2.6 wt % of iron (Fe) was used. The reaction was carried out for 20 days. The conversion was consistently maintained at about 95–100%.

EXAMPLE 9

Hydrogenation was carried out in the same manner as that of Example 7 except that a Raney nickel catalyst for hydrogenation consisting of 53.5 wt % of nickel (Ni), 42.4 wt % of aluminum (Al), 0.1 wt % of iron (Fe), and 4.0 wt % of molybdenum (Mo) was used. The reaction was carried out for 20 days. The conversion was consistently maintained at about 94–100%.

EXAMPLE 10

Hydrogenation was carried out in the same manner as that of Example 7 except that a Raney nickel catalyst for hydrogenation consisting of 47.5 wt % of nickel (Ni), 48 wt % of aluminum (Al), 0.5 wt % of iron (e), 3.0 wt % of manganese (Mn), and 1.0 wt % of cobalt (Co) was used. The reaction was carried out for 20 days. The conversion was consistently maintained at about 90–100%.

COMPARATIVE EXAMPLE 10

Hydrogenation was carried out in the same manner as that of Example 7 except that a Raney nickel catalyst for hydrogenation consisting of 52 wt % of nickel (Ni) and 48 wt % of aluminum (Al) was used. After the reaction was carried out for 1.5 days, the conversion was reduced from 90% to 25%.

COMPARATIVE EXAMPLE 11

Hydrogenation was carried out in the same manner as that of Example 7 except that a Raney nickel catalyst for hydrogenation consisting of 48.7 wt % of nickel (Ni), 48.4 wt % of aluminum (Al), and 2.9 wt % of cobalt (Co) was used. After the reaction was carried out for 1.5 days, the conversion was reduced from 60% to 20%.

COMPARATIVE EXAMPLE 12

Hydrogenation was carried out in the same manner as that of Example 7 except that a E-113T catalyst manufactured by the Mallinckrodt company of USA was used. The E-113T catalyst consists of ⅛" tablets of CuCr. After the reaction was carried out for 4 hours, the conversion was reduced from 10% to 0%.

COMPARATIVE EXAMPLE 13

Hydrogenation was carried out in the same manner as that of Example 7 except that a TYPE:50A catalyst manufactured by the Johnson Matthey company of British was used. The TYPE:50A catalyst consists of 0.5 wt % of Pd based on Al$_2$O$_3$. During the 4 hours of reaction, the conversion was 0% throughout.

The results depicted in Examples 7–10 and Comparative Examples 10–13 are summarized in the table 2 below.

TABLE 2

(with fixed bed reactor)

| | Composition of the Catalyst (wt %) | Period of Reaction | Conversion (%) |
|---|---|---|---|
| Example 7 | Ni:Al:Fe:Cr = (57):(40.2):(0.7):(2.1) | 20 days | 96–100% |
| Example 8 | Ni:Al:Fe = (50.4):(47):(2.6) | 20 days | 95–100% |
| Example 9 | Ni:Al:Fe:Mo = (53.5):(42.4):(0.1):(4) | 20 days | 94–100% |
| Example 10 | Ni:Al:Fe:Mn:Co = (47.5):(48):(0.5):(3):(1.0) | 20 days | 90–100% |
| Comparative Example 10 | Ni:Al = (52):(48) | 1.5 days | reduced from 90% to 25% |
| Comparative Example 11 | Ni:Al:Co = (48.7):(48.4):(2.9) | 1.5 days | reduced from 60% to 20% |
| Comparative Example 12 | CuCr | 4 hours | reduced from 10% to 0% |
| Comparative Example 13 | 2 wt % of Pd based on $Al_2O_3$ | 4 hours | 0% |

What is claimed is:

1. A process for preparing a diol comprising
   hydrogenating at least one hydroxy aldehyde or hydroxy cyclic ether or mixtures thereof with a modified Raney catalyst comprising 40–98 wt % of nickel, 1–50 wt % of aluminum, and 0.05–15 wt % of iron at a temperature of 50° C. to 200° C. and a pressure of 10–200 kg/cm²G.

2. The process according to claim 1, wherein said hydroxy aldehyde is 4-hydroxy-butanal or 2-methyl-3-hydroxypropanal.

3. The process according to claim 1, wherein said hydroxy cyclic ether is 2-hydroxy-tetrahydrofuran.

4. The process according to claim 3, wherein said diol is 1,4-butanediol.

5. The process according to claim 1, wherein said diol is 1,4-butanediol or 2-methyl-1,3-propanediol.

6. A modified Raney nickel catalyst for hydrogenation of hydroxy aldehydes and hydroxy cyclic ethers, consisting essentially of 40–98 wt % of nickel, 1–50 wt % of aluminum, and 0.05–15 wt % of iron.

7. The modified Raney catalyst according to claim 6, wherein said hydroxy aldehyde is 4-hydroxy-butanal or 2-methyl-3-hydroxypropanal.

8. The modified Raney nickel catalyst according to claim 6, wherein the hydroxy cyclic ether is 2-hydroxy-tetrahydrofuran.

9. A process for preparing a diol comprising
   hydrogenating at least one hydroxy aldehyde or hydroxy cyclic ether or mixtures thereof with the modified Raney catalyst according to claim 6 at a temperature of 50° C. to 200° C. and a pressure of 10–200 kg/cm²G.

10. A modified Raney nickel catalyst for hydrogenation of hydroxy aldehydes and hydroxy cyclic ethers, consisting essentially of 40–98 wt % of nickel, 1–50 wt % of aluminum, 0.05–15 wt % of iron, and 0.05–10 wt % of at least one member selected from the group consisting of chromium, molybdenum, tungsten, cobalt, manganese, and a mixture of tungsten and titanium.

11. A process for preparing a diol comprising
    hydrogenating at least one hydroxy aldehyde or hydroxy cyclic ether or mixtures thereof with the modified Raney catalyst according to claim 10 at a temperature of 50° C. to 200° C. and a pressure of 10–200 kg/cm²G.

12. The modified Raney nickel catalyst according to claim 10, wherein said at least one member is selected from the group consisting of chromium, molybdenum, tungsten, cobalt, and manganese.

13. A process for preparing a diol comprising
    hydrogenating at least one hydroxy aldehyde or hydroxy cyclic ether or mixtures thereof with the modified Raney catalyst according to claim 12 at a temperature of 50° C. to 200° C. and a pressure of 10–200 kg/cm²G.

* * * * *